(12) United States Patent  
Metcalfe

(10) Patent No.: US 7,299,587 B1  
(45) Date of Patent: Nov. 27, 2007

(54) METHOD AND APPARATUS FOR CONTROLLING PESTS

(75) Inventor: Colin T. Metcalfe, Acklam (GB)

(73) Assignee: IDA Limited, Darlington (GB)

( * ) Notice: Subject to any disclaimer, the term of this patent is extended or adjusted under 35 U.S.C. 154(b) by 0 days.

(21) Appl. No.: 09/736,023

(22) PCT Filed: Jul. 1, 1999

(86) PCT No.: PCT/GB99/02090

§ 371 (c)(1),  
(2), (4) Date: Dec. 20, 2000

(87) PCT Pub. No.: WO00/01236

PCT Pub. Date: Jan. 13, 2000

(30) Foreign Application Priority Data

Jul. 3, 1998 (GB) .................................. 9814507.1

(51) Int. Cl.  
*A01M 1/10* (2006.01)  
*A01M 1/20* (2006.01)

(52) U.S. Cl. .......................................... 43/121; 43/107

(58) Field of Classification Search .................. 43/107, 43/121, 132.1, 120, 131; 424/405, 421; 206/350, 818  
See application file for complete search history.

(56) References Cited

U.S. PATENT DOCUMENTS

| | | | | |
|---|---|---|---|---|
| 2,167,978 A | * | 8/1939 | Jennerich | |
| 2,225,205 A | * | 12/1940 | Brooks | 206/818 |
| 2,436,607 A | * | 2/1948 | Rosenthal | 206/818 |
| 2,450,400 A | * | 10/1948 | Stevens | 206/818 |
| 2,672,232 A | * | 3/1954 | Kessell, Jr. | 206/350 |
| 2,888,136 A | * | 5/1959 | La Borde | 206/350 |
| 3,056,724 A | * | 10/1962 | Marston | 424/438 |
| 3,067,903 A | * | 12/1962 | Jones, Jr. | 206/818 |
| 3,162,573 A | * | 12/1964 | Geary | 424/486 |
| 3,269,528 A | * | 8/1966 | Leedy | 206/350 |
| 3,274,052 A | * | 9/1966 | Yaffe et al. | 424/421 |
| 3,480,145 A | * | 11/1969 | Gladden | 206/818 |
| 3,587,835 A | * | 6/1971 | Shore | 206/350 |
| 3,704,777 A | * | 12/1972 | Linnebuhr | 206/350 |
| 3,704,991 A | * | 12/1972 | Leedy | 206/350 |
| 3,726,803 A | * | 4/1973 | Bayless et al. | 424/492 |
| 3,731,415 A | * | 5/1973 | Shore | 206/350 |

(Continued)

FOREIGN PATENT DOCUMENTS

WO    WO 94 00980 A    1/1994

(Continued)

OTHER PUBLICATIONS

Definition of "Inert Ingredients" from EPA Pesticide Glossary, Available web site: http://environment.about.com/cs/pesticides/g/inertingred.htm, Accessed on: Apr. 11, 2005.*

(Continued)

*Primary Examiner*—Darren W. Ark  
(74) *Attorney, Agent, or Firm*—Bacon & Thomas, PLLC

(57) ABSTRACT

A method of controlling pests, such as insects, by trapping and/or killing them wherein at least a part of a pest to be trapped or killed is exposed a composition comprising particles containing or consisting of at least one magnetic material.

22 Claims, 3 Drawing Sheets

U.S. PATENT DOCUMENTS

| | | | | |
|---|---|---|---|---|
| 3,921,983 A * | 11/1975 | Taylor | ................... | 206/818 |
| 4,044,495 A * | 8/1977 | Nishimura et al. | ............ | 43/114 |
| 4,045,291 A * | 8/1977 | Berger | ................... | 206/818 |
| 4,058,209 A * | 11/1977 | Schmidt | ................... | 206/350 |
| 4,169,532 A * | 10/1979 | Scapellati | ................... | 206/818 |
| 4,263,740 A * | 4/1981 | Hemsarth et al. | ............. | 43/114 |
| 4,331,335 A * | 5/1982 | Starkweather | ............. | 206/350 |
| 4,423,564 A * | 1/1984 | Davies et al. | ................. | 43/121 |
| 4,569,462 A * | 2/1986 | Belokin | ................... | 206/818 |
| 4,657,543 A * | 4/1987 | Langer et al. | ............. | 424/486 |
| 4,911,981 A * | 3/1990 | Schnur et al. | ......... | 428/402.24 |
| 4,928,823 A * | 5/1990 | Campbell | ................... | 206/818 |
| 5,000,960 A * | 3/1991 | Wallach | ................... | 424/1.21 |
| 5,069,339 A * | 12/1991 | Hsu | ................... | 206/818 |
| 5,091,188 A * | 2/1992 | Haynes | ................... | 424/405 |
| 5,102,662 A * | 4/1992 | Gallagher | ................... | 424/405 |
| 5,141,744 A * | 8/1992 | Chang et al. | ................ | 424/84 |
| 5,145,063 A * | 9/1992 | Lee | ................... | 206/818 |
| 5,162,014 A * | 11/1992 | Moore et al. | ................... | 449/2 |
| 5,201,444 A * | 4/1993 | Simonet | ................... | 224/183 |
| 5,213,240 A * | 5/1993 | Dietz et al. | ................... | 224/183 |
| 5,240,259 A * | 8/1993 | O'Grady | ................... | 206/350 |
| 5,277,431 A * | 1/1994 | O'Grady | ................... | 206/350 |
| 5,354,563 A * | 10/1994 | Toyotama | ................... | 424/489 |
| 5,405,004 A * | 4/1995 | Vest et al. | ................... | 206/350 |
| 5,417,976 A * | 5/1995 | Peery et al. | ................. | 424/438 |
| 5,492,696 A * | 2/1996 | Price et al. | ................. | 424/405 |
| 5,526,927 A * | 6/1996 | McLemore | ................ | 206/818 |
| 5,527,524 A * | 6/1996 | Tomalia et al. | ............ | 424/405 |
| 5,543,158 A * | 8/1996 | Gref et al. | ................. | 424/501 |
| 5,565,215 A * | 10/1996 | Gref et al. | ................. | 424/501 |
| 5,686,113 A * | 11/1997 | Speaker et al. | ............ | 424/490 |
| 5,693,321 A * | 12/1997 | Klaveness et al. | ........ | 424/78.37 |
| 5,728,376 A * | 3/1998 | Attygalle et al. | ............. | 424/84 |
| 5,771,628 A * | 6/1998 | Nobbs | ................... | 43/121 |
| 5,837,273 A * | 11/1998 | Shasha et al. | .............. | 424/405 |
| 5,888,500 A * | 3/1999 | Marshall | ................... | 424/405 |
| 5,941,010 A * | 8/1999 | Latwesen | ................... | 43/4.5 |
| 5,985,660 A * | 11/1999 | Galy | ................... | 435/372 |
| 6,007,845 A * | 12/1999 | Domb et al. | ................ | 424/501 |
| 6,041,543 A * | 3/2000 | Howse | ................... | 43/121 |
| 6,123,965 A * | 9/2000 | Jacob et al. | ................ | 424/489 |
| 6,156,348 A * | 12/2000 | Santos et al. | ............... | 424/501 |
| 6,176,033 B1 * | 1/2001 | Latwesen | ................... | 43/4.5 |
| 6,216,384 B1 * | 4/2001 | Dickson et al. | ............... | 43/131 |
| 6,315,120 B1 * | 11/2001 | Tally et al. | ................. | 206/350 |
| 6,327,810 B1 * | 12/2001 | Howse | ................... | 43/107 |
| 6,401,253 B2 * | 6/2002 | Brunson | ................... | 206/818 |
| 6,413,548 B1 * | 7/2002 | Hamer et al. | ............... | 424/489 |
| 6,974,048 B2 * | 12/2005 | Funk | ................... | 206/818 |
| 2001/0021703 A1 * | 9/2001 | Kosak | ................... | 424/450 |
| 2001/0026802 A1 * | 10/2001 | Price et al. | ................. | 424/405 |
| 2004/0200128 A1 * | 10/2004 | Metcalfe | ................... | 43/107 |
| 2006/0051388 A1 * | 3/2006 | Howse et al. | ............... | 424/417 |

FOREIGN PATENT DOCUMENTS

WO     WO 97 33472 A     9/1997

OTHER PUBLICATIONS

Periodic Table: Transition Metals At Chemical Elements.com, Available web site: www.chemicalelements.com/groups/transition.html, Accessed on: Apr. 11, 2005.*

Cobalt Oxide (Co3O4)—Low Sodium Electronic Grade, Available web site: www.atomixinc.com/cobaltoxide.htm, Accessed on: Apr. 13, 2005.*

Magnetic Nanoparticles/Nanostructures, Available web site: www.reade.com/Products/Nanomaterials/magnetic-nanoparticle.html, Accessed on: Apr. 13, 2005.*

* cited by examiner

METHOD AND APPARATUS FOR CONTROLLING PESTS

The present invention relates to a method and apparatus for controlling pests by trapping or killing them and is particularly concerned with the control of flying or crawling insects.

The most common domestic insect pests are houseflies, mosquitoes and cockroaches.

The common housefly, *Musca comestica*, occurs throughout the world in domestic situations. Together with similar species, such as, the lesser housefly, blowflies and flesh flies, it contaminates food and spreads diseases, such as, typhoid and cholera, and also carries the eggs of parasitic worms.

The housefly is also a problem on refuse tips and is becoming a progressively greater nuisance in agriculture, where it breeds in deep litter breeding units for poultry and other animals.

The cockroach is ubiquitous in urban situations in the tropics and sub-tropics and is common in heated buildings in Europe and North America where food is prepared. Large cockroach populations are found in sewers and drains and many disease organisms have been isolated from them.

The mosquito is both a severe nuisance pest and vastly important as a vector for blood-borne diseases, such as, malaria, yellow fever and dengue.

Control of such insect pests is becoming more urgent as human populations increase and provide more resources for them to breed.

Insecticide use inevitably encourages the evolution of resistance. In the United Kingdom as in many other countries, prolonged attempts to control houseflies in animal rearing system have led to the increasing incidence of flies which are resistant to the major insecticides in common use.

Control of insects in areas where food is prepared depends upon scrupulous hygienic procedures, periodic fumigation with insecticides and/or the use of traps.

There is increasing public pressure throughout Europe for the development of environmentally acceptable pest control measures in which synthetic insecticides are not used.

WO94/00980 describes a method of controlling pests, such as insects, involving the use of electrostatically charged powders, in which the powders are used to adhere to the insect cuticle and also act as carriers for pesticides or other biologically active compounds. The electrostatically charged particles also adhere to the feet of the insects, blocking the mechanism by which they grip surfaces thereby making it possible to trap the insects as they slide down an inclined surface.

The disadvantages of the use of electrostatically charged particles is that they must be charged before use, for example by friction, and they lose their charge rapidly in conditions of high humidity and when moisture films develop. Furthermore, the particles are removed from bait stations or traps by wind currents, or by shaking.

We have now developed a method and apparatus for controlling pests which involves the use of particles which are permanently magnetised and are not affected by moisture or humidity and which, when anchored on a conducting or magnetic surface, will remain in position for long periods of time without losing their effectiveness. Although electrostatically charged particles adhere to the cuticles of insects, it is surprising that ferromagnetic particles also adhere to the cuticles of insects and this is a surprising and unexpected effect.

Accordingly, the present invention provides a method of controlling pests, such as insects, by trapping and/or killing them wherein at least a part of a pest to be trapped or killed is exposed to a composition comprising particles containing or consisting of at least one magnetic material.

In carrying out the method of the present invention the pests are exposed to particles which either contain or consist wholly of a magnetic material, such as a ferromagnetic oxide. Ferromagnetic oxides are often termed ferrites which is a generic term describing a class of magnetic oxide compounds that contain iron oxide as a primary component. The spinel ferrites have the general composition $MFe_2O_4$ and are isostructural with the mineral spinel, $MgAl_2O_4$. M in the formula is generally Mg, Mn, Co, Ni, Zn or Cu, or mixtures thereof. A second group of ferrites is the hexagonal ferrites which are a group of ferromagnetic oxides in which the principal component is $Fe_3O_3$ in combination with a divalent metal oxide such as BaO, SrO or PbO and a divalent transition-metal oxide. A third group of ferrites is the garnets which have the general structure $M_3Fe_5O_{12}$. The metal M may be, for example, Y, La, Ca, the rare earth metals or other large cations.

Preferred materials for use in the present invention are strontium ferrite which is a hard magnetic material, optionally in admixture with a ferrosilicate or neodymium barium salts. Soft magnetic materials, such as Fe, $Fe_2O_3$ or ferrosilicates may also be used if they have been magnetised or become magnetised on admixture with hard magnetic materials.

The particles which are used in the present invention preferably have an average particle size diameter in the range of from 2 to 100 micrometres, preferably 3 to 50 micrometres. Generally the particles are applied to a surface in an area in which pests are present.

The composition which is used in the present invention may consist wholly of the magnetic particles. Alternatively, the composition may compromise a proportion of the magnetic material in admixture with one or more other components. For example, the magnetic particles may be admixed with one or more filler materials such as talc, silicon dioxide, diatomaceous earth, ferrosilicates and the like. Alternatively, the magnetic particles may be admixed with particles which contain one or more pesticides or behaviour modifying chemicals or the magnetic particles may be coated with one or more pesticides or behaviour modifying chemicals. Generally, the magnetic particles will comprise at least 10% of the composition, preferably at least 50% by weight of the composition.

Insects adhere to smooth or inclined surfaces using adhesive organs on their feet. These organs are pads covered with numerous fine hairs with flattened tips. An oily substance is secreted onto the tips of the hairs and surface molecular forces ensure adhesion of the hairs to the surface on which the insect is standing. Accordingly, as the feet of an insect become covered in particles, the insect loses its ability to adhere to a smooth and, in particular, to an inclined surface. Furthermore, the particles also interfere with the insect's sense organs, which may cause the insect to groom more frequently.

In the case of flying insects, it is known that the flight reflex is inhibited by contact of the feet is with any substrate. Accumulation of the particles on the insect's feet tend to inhibit the flight and the adhesion of the insect which is thus more likely to fall from an inclined surface. Accordingly, a flying insect having landed on a suitably coated and inclined surface is thus unlikely to fly away and simply will slide down the surface.

The magnetic particles which are used in the method of the present invention may consist solely of the magnetic material. Alternatively, the particles may be composite particles which comprise a core of an inert substrate which is impregnated with and/or coated with the magnetic material. The inert substrate is a material which acts as a carrier for the magnetic material and which is chemically and biologically inert. Examples of suitably inert substrates for use in the present invention are silicon dioxide, magnesium silicate (talc), diatomaceous earth, cellulose or natural or synthetic polymers such as chitin, chitosan or rubber, or aerogels.

The inert substrate may additionally have a pesticide or a behaviour modifying chemical impregnated thereon or associated therewith, for example by adsorption thereon. The amount of pesticide or behaviour modifying chemical which is impregnated into or associated with the inert substrate will generally comprise at least 0.1% by weight of the inert substrate. The amount of the pesticide or behaviour modifying chemical will depend upon the intended release rate from the composition and the length of intended duration of release.

The pesticide which may be incorporated into the composite particles or incorporated into the composition used in the invention may be specifically targeted to the control of particular pests. For example, an insecticide may be applied to sexually mature male insects so that it spreads amongst the rest of the population during mating, or by contact during swarming. The insecticide is unlikely to spread to other species of insect when transmitted in this way.

Each pesticide may be chosen to have a narrow spectrum of action. Entomopathogens are particularly well suited to this. A further embodiment is to use a behaviour modifying chemical, for example a specific attractant to attract insects to the particles. For example, the attractant may be a sexual pheromone. Furthermore, a sexual attractant pheromone may be used to produce male confusion. This technique depends on the very high sensitivity of male insects to volatile sex attractants produced by females of the same species.

As the insects contact the magnetic particles the particles are picked up by the insect from the surface on which the particles are located. The particles are then transferred to the body parts of the insect by movement and during grooming. The particles remain in place and continue to release the pesticide or behaviour modifying chemical, such as a pheromone. Accordingly, the composite particles which may be used in the method of the present invention have a dual effect. Not only does the magnetic material impregnated into or coated onto the inert substrate have an effect on the orientation and stability of the insects, but the pesticide or behaviour modifying chemical will produce a second effect which is associated with the particular nature of the pesticide or behaviour modifying chemical incorporated into the composite particles.

It will be understood that by the term "pesticide" as used therein is meant any substance which can be used in the control of agricultural, natural environmental and domestic pests, such as insects. Included within this term, therefore, are naturally occurring or synthetic chemical insecticides, fungicides, acaricides, insect growth regulators and chemosterilants; entomopathogens such as bacteria, viruses and fungi. The term "behaviour modifying chemicals" includes within its scope the pheromones, allomones, kairomones, parapheromones and food odours.

The present invention furthermore includes within its scope a first pesticidal composition in particulate form which comprises composite particles each comprising a core of an inert substrate having a pesticide or behaviour modifying chemical impregnated thereon or associated therewith and the core being impregnated or coated with a ferromagnetic oxide. The composite particles are as described above in relation to the method of the invention.

The present invention still further includes within its scope a second pesticidal composition in particulate form which comprises particles containing or consisting of a magnetic material in admixture with particles which contain or consist of one or more pesticides or behaviour modifying chemicals.

Furthermore, in a further embodiment of the present invention provides an insect trap which comprises a housing, a zone of the housing or a zone within the housing comprising a magnetically polarized material and the said zone being coated with a composition comprising particles containing or consisting of a magnetic material of opposite polarity to that of the magnetically polarized material.

The insect trap of the present invention has a zone of magnetically polarized material which may form a portion of one or more walls of the housing, or may be provided as a separate insert within the housing. The zone of the magnetically polarized material may be formed, for example from a plastic material which is impregnated with a ferromagnetic oxide which is magnetically polarized. Alternatively, the zone may itself be formed solely from the magnetically polarized material. The zone of the magnetically polarized material has an opposite polarity to the polarity of the magnetic material which is coated onto the said zone. Preferably the zone has a surface which is inclined to the horizontal and, as described above, this will assist in disrupting the orientation of the insects which walk or crawl over the zone.

The insect trap may include a trapping zone into which the insects fall when they become established after contact with the particles containing or consisting of the magnetic material. The trapping zone may include a fluid, a powder, a desiccant, a chemical toxicant or an adhesively sticky or tacky surface, or any combination thereof, for retaining the insects therein.

The immobilised and trapped insects may be left to die or they may be removed for destruction or study.

The insect trap of the present invention may be provided with means to lure the insects into the housing. Insect lures are well known and may comprise, for example, a light source with some emission in the ultraviolet range, or a chemical stimulant such as a natural or synthetic pheromone attractant, or an odour normally associated with the insects' food or food plant.

It will be appreciated that the insect traps of the present invention can be produced cheaply and insect destabilization and knock down may be achieved without the use of electrical grids. Pollution problems arising from the use of toxic chemicals are eliminated or greatly reduced because any pesticide contained in the composite particles which may be used in the present invention are applied only in the area of the trap and not generally to the location of the pest. The trap may be recharged with additional magnetic powder when the original powder charge has been used up by insects contacting the powder. Furthermore, when the trap of the present invention is used with composite particles which also incorporate a pesticide or a behaviour modifying chemical then the present invention provides an efficient method of killing insects by ensuring that the pesticide reaches the insects more effectively and remains in place for longer periods, or alternatively provides a means by which the behaviour of the insects is disrupted, thereby disrupting the mating and reproductive cycles of the insects.

The present invention will be further described with reference to the accompanying drawings in which:—

Figure 1A:
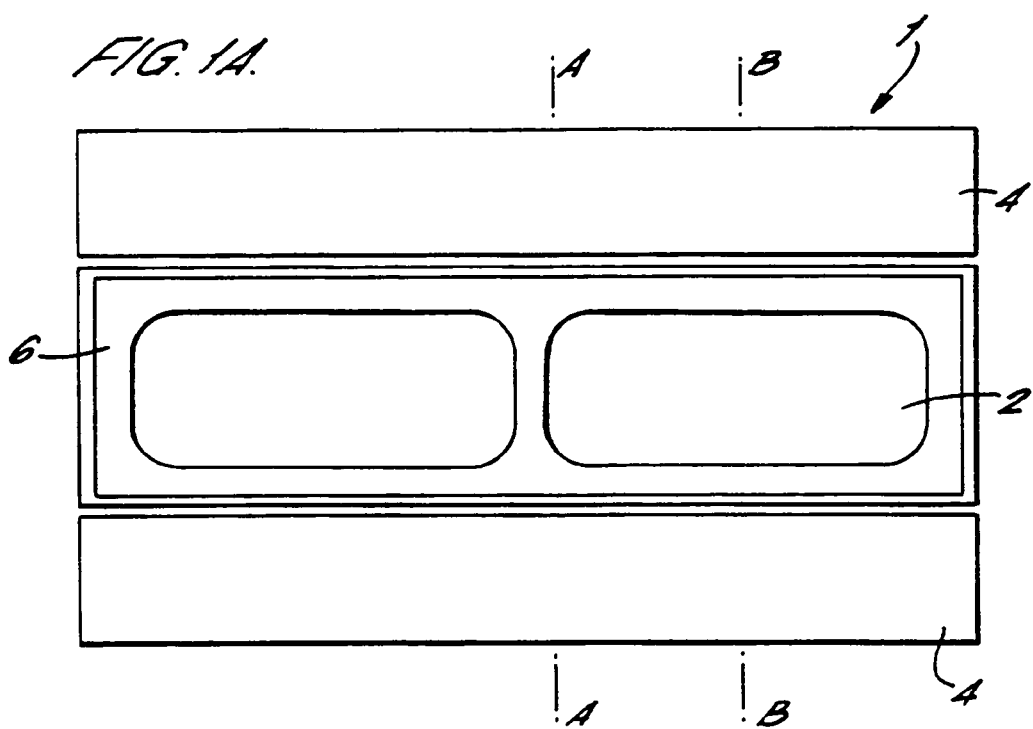
FIG. 1A is a plan view of an insect trap in accordance with the present invention.
Figure 1B:
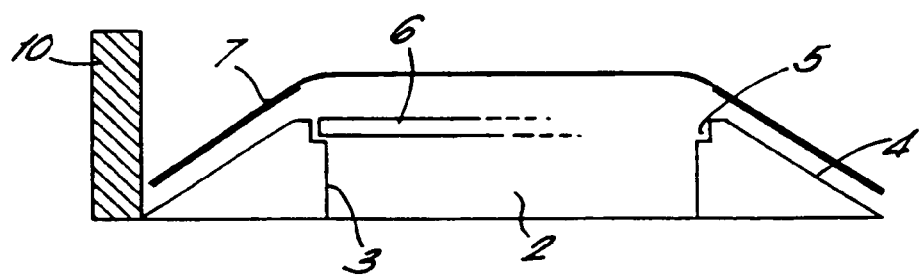
FIG. 1B is a cross section along the line A-A of the trap of FIG. 1A with a lid positioned thereover.
Figure 1C:
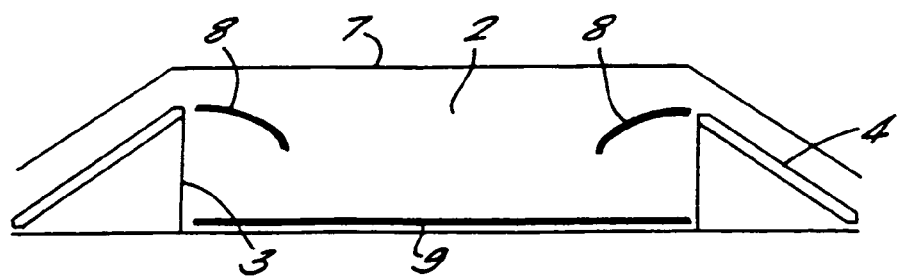
FIG. 1C is a cross section along the line B-B of the trap of FIG. 1A with a lid positioned thereover.

Referring to the drawings, a cockroach trap is illustrated in FIGS. 1A, 1B and 1C. The trap comprises an elongate body 1 having a trapping area 2 formed in the centre thereof. The trapping area 2 is bounded on two sides thereof by two longitudinally extending walls 3 which are of a sufficient height to prevent the cockroaches from climbing over them. Ramped surfaces 4 extend downwardly from the tops of each of the walls. The top edges of the longitudinally extending walls 3 are provided with recesses 5 which are designed to support an elongate bridging plate 6. The bridging plate 6 is constructed from a plastic material containing a proportion of a ferromagnetic material to make it weakly magnetic. The top surface of bridging plate 6 is dusted with a ferromagnetic powder.

As shown in FIGS. 1B and 1C the trap has a lid 7 which is held in place by magnetic studs (not shown) positioned at the ends of the ramped surfaces 4.

An odorous attractant is placed in the trapping area 2. A cockroach attracted by the attractant walks up the ramped surface and then onto the bridging plate 6. The bridging plate has inwardly curved surfaces 8. When the cockroach walks on the surface of the plate 6 the magnetic powder with which the plate 6 is coated adheres to the cockroach's feet, blocking the insect's adhesive pads and causing it to slip down the curved surface 8 into the trapping area 2. The trapping area may be provided with a glue pad 9 to which the cockroach becomes adhered.

The opening between the ramped surface 4 and the lid 7 is such that a cockroach can climb up the ramped surface, for example when the trap is placed adjacent a wall 10.

When the trap is full of cockroaches, it may be closed by pushing the lid off the magnetic studs. The trap can then be emptied for reuse, or disposed of.

The present invention will be further described with reference to the following Examples.

EXAMPLE 1

A surface was coated with a composition comprising 10% by weight of strontium ferrite and 90% by weight of a ferrosilicate. The particles had an average particle diameter in the range of from 5 to 100 micrometres. Houseflies (*Musca domestica*) were allowed to walk over the surface of the powder for 3 to 5 minutes after which the powder coating was spread over most of their body parts by their own grooming activities. They continued grooming whilst trying to dislodge the particles and were unable to walk on a sloping plastic surface without slipping with every movement. This behaviour continued for 4 days until all of the flies were dead. A coating of the powder was clearly visible on their wings and bodies. A similar result was obtained using cockroaches (*Blattella germanica*).

EXAMPLE 2

Figure 2:
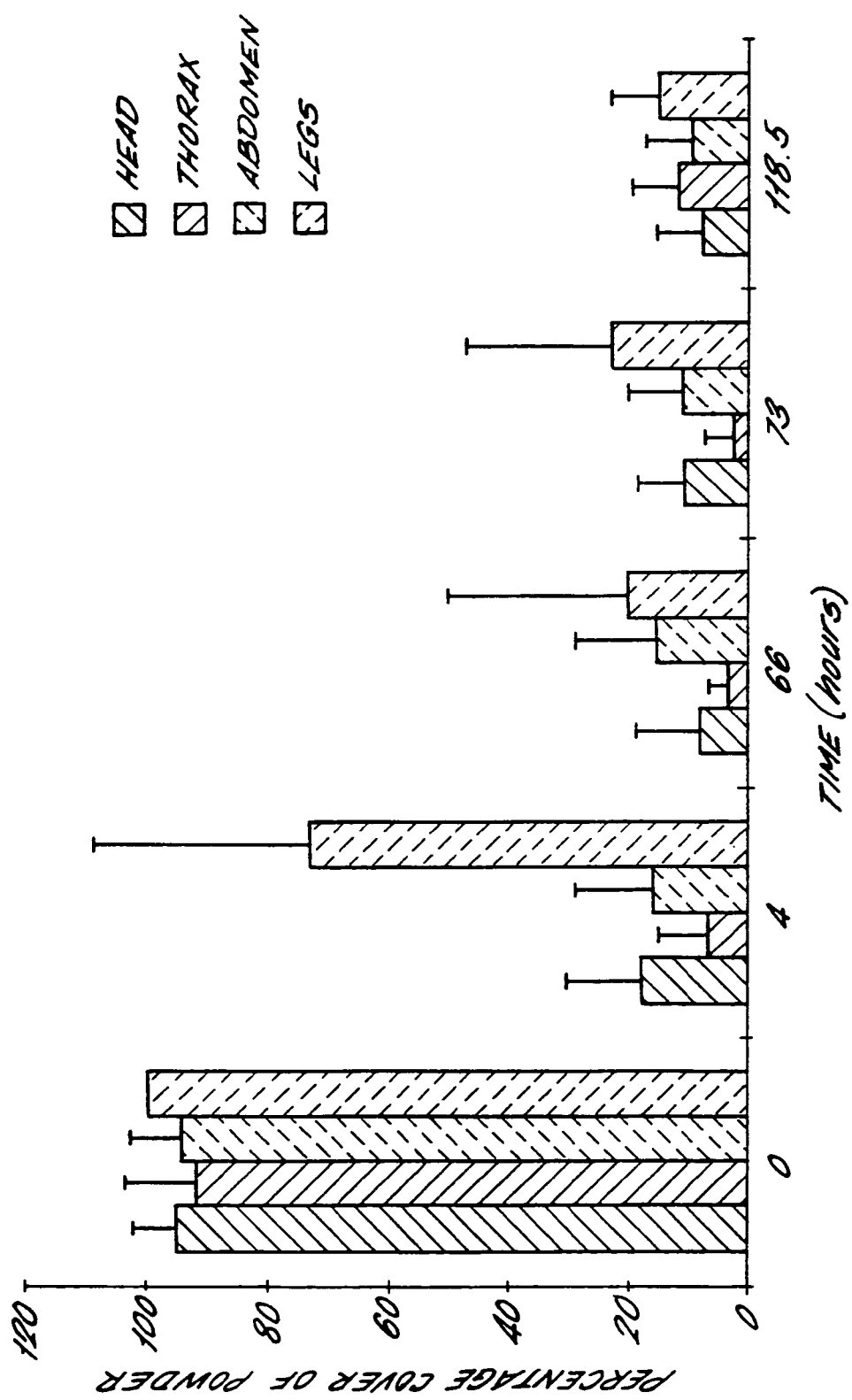
FIG. 2 illustrates the percentage coverage of powder on the body parts of *Blattella germanica* over time as described in Example 2 herein below.

Adult cockroaches (*Blattella germanica*) were exposed to the ferromagnetic oxide powder as described in Example 1 and the density of the particles on the thorax was determined by sacrificing ten insects at intervals of up to 178.5 hours and counting the particles under the microscope. The results are given in FIG. 2 which shows an initial exponential loss rate of the powder (mainly larger particles) after which the density of the powder on the surface of the insects remains fairly constant.

EXAMPLE 3

Figure 3:
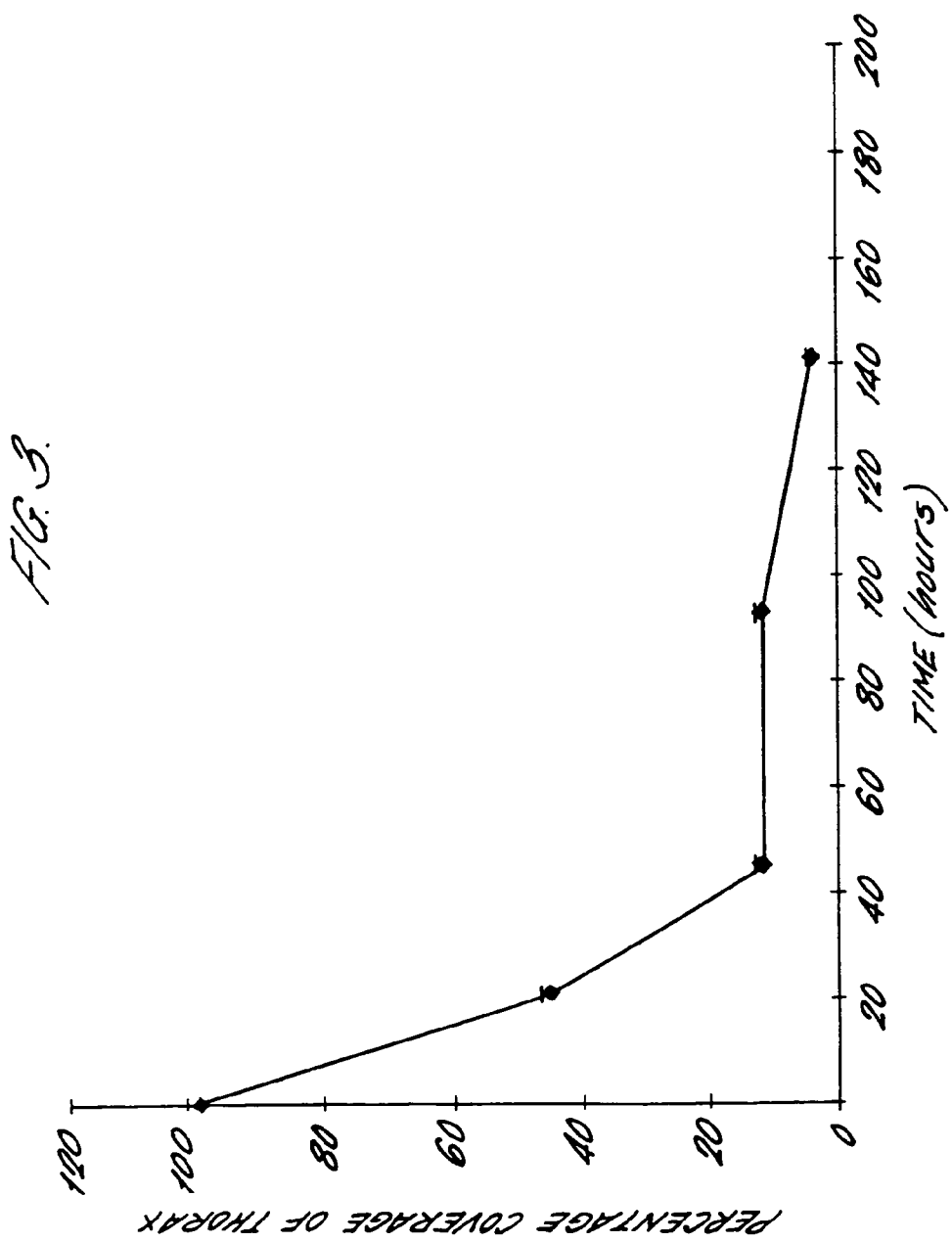
FIG. 3 illustrates the loss of magnetic powder from the bodies of cockroaches over time.

The procedure of Example 1 was repeated using strontium ferrite powder. The loss of powder with time is plotted in FIG. 3. It can be seen that after an initial decline in the amount of powder remaining attached to the cockroach's bodies, a fairly steady state is reached after about 60 minutes with only a further slight tailing off with time.

The invention claimed is:

1. An insect trap comprises a housing having an entrance open to the ambient and allowing access to an interior of the housing, a zone of the housing or a zone within the housing comprising a magnetically polarized material and the zone being coated with a composition suitable for adhering to insects including particles comprising a magnetic material of opposite polarity to that of the magnetically polarized material;

wherein the particles have an average particle size diameter in the range of 2 to 100 μm.

2. An insect trap as claimed in claim 1 wherein the zone of the magnetically polarized material is formed by a portion of at least one wall of the housing.

3. An insect trap as claimed in claim 1 wherein the zone of the magnetically polarized material comprises a removable insert placed within the housing.

4. An insect trap as claimed in claim 1 wherein the zone has a surface which is inclined to the horizontal.

5. An insect trap as claimed in claim 1 wherein the magnetic material is a ferromagnetic oxide.

6. An insect trap as claimed in claim 1 wherein particles further comprise a pesticidal composition.

7. An insect trap according to claim 1, wherein the composition consists of the magnetic particles.

8. A method of trapping insects with an insect trap having a housing defining an entrance open to the ambient and allowing access to an interior of the housing and a trapping area disposed below the entrance, the method comprising the step of:

coating a zone of or within the housing with a composition including particles comprising a magnetic material, inducing an insect in contact with the composition to become at least partially coated with the composition and destabilized, thereby falling into the trapping area;

wherein the particles have an average particle size diameter in the range of 2 to 100 μm.

9. A method as claimed in claim 8 wherein the magnetic material is a ferromagnetic oxide.

10. A method as claimed in claim 8 wherein the particles are applied to a surface in an area of the zone of or within the housing in which pests are present.

11. A method as claimed in claim 10, wherein said surface is inclined to the horizontal.

12. A method as claimed in claim 8 wherein the composition comprises at least 10% by weight of magnetic particles.

13. A method as claimed in claim 8 wherein a pesticide or behavior modifying chemical is admixed with the particles of the magnetic material.

14. A method as claimed in claim 8 wherein a pesticide or behavior modifying chemical is coated onto the particles of the magnetic material.

15. A method as claimed in claim 8 wherein the particles are composite particles which each comprise a core of an inert substrate which is impregnated with and/or coated with the magnetic material.

16. A method as claimed in claim 15 wherein the core comprises silicon dioxide, magnesium silicate, diatomaceous earth, cellulose or a natural or synthetic polymer.

17. A method as claimed in claim 15 wherein the inert substrate has a pesticide or behavior modifying chemical impregnated thereon or associated therewith.

18. A method as claimed in claim 17 wherein the pesticide is an insecticide, fungicide, acaricide, insect growth regulator or chemosterilant.

19. A method as claimed in claim 17 wherein the pesticide is a bacterium, virus or fungus.

20. A method as claimed in claim 17 wherein the behavior modifying chemical is a pheromone.

21. A method as claimed in claim 17 wherein the pesticide or behavior modifying chemical comprises at least 0.1% by weight of the cores of the particles.

22. The method according to claim 8, wherein the composition consists of the magnetic particles.

* * * * *